US006274330B1

(12) United States Patent
Segerson et al.

(10) Patent No.: US 6,274,330 B1
(45) Date of Patent: Aug. 14, 2001

(54) L-AP4 SENSITIVE GLUTAMATE RECEPTORS

(75) Inventors: Thomas P. Segerson; J. Mark Kinzie, both of Portland, OR (US); Eileen R. Mulvihill, Mercer Island, WA (US); Julie A. Saugstad; Gary L. Westbrook, both of Portland, OR (US)

(73) Assignees: ZymoGenetics, Inc.; State of Oregon, acting by and through the Oregon State Board of Higher Education on behalf of the Oregon Health Sciences University, both of Portland, OR (US)

(*) Notice: Subject to any disclaimer, the term of this patent is extended or adjusted under 35 U.S.C. 154(b) by 0 days.

(21) Appl. No.: 08/176,401

(22) Filed: Dec. 30, 1993

(51) Int. Cl.[7] ......................... G01N 33/53; C07K 14/705; C12N 15/12
(52) U.S. Cl. ..................... 435/7.2; 435/69.1; 435/252.3; 435/320.1; 530/350; 536/23.5
(58) Field of Search ............................. 435/69.1, 252.3, 435/320.1, 7.2; 530/350; 536/23.5

(56) References Cited

U.S. PATENT DOCUMENTS

| 5,089,386 | 2/1992 | Stackebrandt et al. ................. 435/6 |
| 5,202,257 | 4/1993 | Heinemann et al. ............ 435/252.3 |

FOREIGN PATENT DOCUMENTS

| 0 569 240 A1 | 11/1993 | (EP) . |
| 569240 | 11/1993 | (EP) . |
| 0 600 278 A2 | 6/1994 | (EP) . |
| 92/10583 | 6/1992 | (WO) . |
| 95/08627 | 3/1995 | (WO) . |

OTHER PUBLICATIONS

George et al. Macromolecular Sequencing and Synthesis, Alan R. Liss, Inc. pp. 127–149, 1988.*

Koerner and Cotman, "Micromolar L–2–amino–4–phosphonobutyric Acid Selectively Inhibits Perforant Path Synapses from Lateral Entorhinal Cortex", Brain Res. 216:192–198 (1981).

Houamad et al., "Expression of Functional GABA, Glycine and Glutamate Receptors in Xenopus Oocytes Infected with Rat Brain mRNA", Nature 310: 318–321, (Jul., 1984).

Nicoletti et al., "Coupling of Inositol Phospholipid Metabolism with Excitatory Amino Acid Recognition Sites in Rat Hippocampus", J. Neurochem. 46: 40–46 (1986).

Sugiyama et al., "A New Type of glutamate Receptor Linked to Inositol Phospholipid Metabolism", Nature 325: 531–533 (Feb., 1987).

Hirono et al., "Characterization of Glutamate Receptors Induced in Xenopus Oocytes After Injection of Rat Brain mRNA", Neurosci. Res. 6: 106–114, (1988).

Snutch, "The Use of Xenopus Oocytes to Probe Synaptic Communication", Trends In Neurosci 11(6): 250–256, (1988).

Fong et al., "Properties of Two Classes of Rat Brain Acidic Amino Acid Receptors Induced by Distinct mRNA Populations in Xenopus Oocytes", Synapse 2: 657–665, (1988).

Recasens et al., "A New Quisqualate Receptor Subtype (sAA$_2$) Responsible for the Glutamate–induced Inositol Phosphate Formation in Rat Brain Synaptoneurosomes", Neurochem. Int. 13: 463–467 (1988).

Sugiyama et al., "Glutamate Receptor Subtypes May be Classified into Two Major Categories: A Study on Xenopus Oocytes Injected with Rat Brain mRNA", Neuron 3: 129–132, (Jul., 1989).

Hollmann et al., "Cloning by Functional Expression of a Member of the Glutamate Receptor Family", Nature 342: 643–648, (Dec., 1989).

Nawy and Jahr, "Suppression by Glutamate of cGMP–activated Conductance in Retinal Bipolar Cells", Nature 346: 269–271 (Jul., 1990).

Sommer et al., "Flip and Flop: A Cell–Specific Functional Switch in Glutamate–Operated Channels of the CNS", Science 249: 1580–1585, (Sep., 1990).

Charpak et al., "Potassium Conductances in Hippocampal Neurons Blocked by Excitatory Amino–acid Transmitters", Nature 347: 765–767 (Oct., 1990).

Schoepp et al., "Pharmacological and Functional Characteristics of Metabotropic Excitatory Amino Acid Receptors", Trends Pharm. Sci., 11:508–515 (Dec., 1990).

Lester and Jahr, "Quisqualate Receptor–Mediated Depression of Calcium Currents in Hippocampal Neurons", Neuron 4: 741–749 (May, 1990).

Masu et al., "Sequence and Expression of a Metabotropic Glutamate Receptor", Nature 349: 760–765 (Feb., 1991).

Houamed et al., "Cloning, Expression, and Gene Structure of a G Protein–Coupled Glutamate Receptor from Rat Brain", Science 252: 1318–1321 (May, 1991).

Baskys and Malenka, "Agonists at Metabotropic Glutamate Receptors Presynaptically Inhibit EPSCs in Neonatal Rat Hippocampus", J. Physiol. (Lond.) 444: 687–701 (1991).

Linden et al., "A Long–Term Depression of AMPA Currents in Cultured Cerebellar Purkinje Neurons", Neuron 7: 81–89 (Jul., 1991).

(List continued on next page.)

Primary Examiner—John Ulm
(74) Attorney, Agent, or Firm—Townsend and Townsend and Crew LLP

(57) ABSTRACT

Metabotropic receptor mGluR7 is identified and sequenced. The mGluR7 receptor subfamily mediates inhibition of transmitter release at selected glutamatergic synapses. The receptors, mGluR7-specific peptides and antibodies thereto are used to identify agonists and antagonists of G protein coupled glutamate receptor mediated neuronal transmitter release, as well as in methods of diagnosis and therapy.

14 Claims, 4 Drawing Sheets

OTHER PUBLICATIONS

Abe et al., "Molecular Characterization of a Novel Metabotropic Glutamate Receptor mGluR5 Coupled to Inositol Phosphate/Ca$^{2+}$ Signal Transduction", *J. Biol. Chem.* 267: 13361–13368 (Jul., 1992).

Tanabe et al., "A Family of Metabotropic Glutamate Receptors", *Neuron* 8: 169–179 (Jan., 1992).

Trombley and Westbrook, "L–AP4 Inhibits Calcium Currents and Synaptic Transmission via a G–Protein–coupled Glutamate Receptor", *J. Neurosci.* 12: 2043–2050 (Jun., 1992).

Thomsen et al., "L–2–Amino–4–phosphonobutyrate (L–AP4) is an Agonist at the Type IV Metabotropic Glutamate Receptor Which is Negatively Coupled to Adenylate Cyclase", *Eur. J. Pharmacol.* 227: 361–362 (1992).

Bashir et al., "Induction of LTP in the Hippocampus Needs Synaptic Activation of Glutamate Metabotropic Receptors", *Nature* 363: 347–350 (May, 1993).

Nakajima et al., "Molecular Characterization of a Novel Retinal Metabotropic Glutamate Receptor mGluR6 with a High Agonist Selectivity for L–2–Amino–4–phosphonobutyrate", *J. Biol. Chem.* 268: 11868–11873 (Jun., 1993).

Sahara and Westbrook, "Modulation of Calcium Currents by a Metabotropic Glutamate Receptor Involves Fast and Slow Kinetic Components in Cultured Hippocampal Neurons", *J. Neurosci.* 13: 3041–3050 (Jul., 1993).

O'Hara et al., "The Ligand–Binding Domain in Metabotropic Glutamate Receptors is Related to Bacterial Periplasmic Binding Proteins", *Neuron* 11:41–52 (Jul., 1993).

Schoepp and Conn, "Metabotropic Glutamate Receptors in Brain Function and Pathology", *Trends Pharmacol. Sci.* 14: 13–20 (Jan., 1993).

Tanabe et al., "Signal Transduction, Pharmacological Properties, and Expression Patterns of Two Rat Metabotropic Glutamate Receptors, mGluR3 and mGluR4", *J. Neurosci.* 13: 1372–1378 (1993).

Okamoto et al., "Molecular Characterization of a New Metabotropic Glutamate Receptor mGluR7 Coupled to Inhibitory Cyclic AMP Signal Transduction", *J. Biol. Chem.* 269:1231–1236 (Jan. 14, 1994).

*New England Biolabs Catalog*, Beverly, MA, USA, p. 82 (1986).

Nakanishi, "Molecular Diversity of Glutamate Receptors and Implications for Brain Function", *Science* 258:597–603 (Oct. 23, 1992).

Gregor et al., "Chromosomal Localization of Glutamate Receptor Genes: Relationship to Familial Amyotrophic Lateral Sclerosis and Other Neurological Disorders of Mice and Humans", *Proc. Natl. Acad. Sci. USA* 90:3053–3057 (Apr., 1993).

Puranam et al., "Chromosomal Localization of Gene for Human Glutamate Receptor Subunit–7", *Somatic Cell and Molecular Genetics*, 19:581–588 (Nov., 1993).

* cited by examiner ctacagaagtccctggcttcccccaaaggagctcacctccagaagcccaccagcataccctccagcgccgccgccgcgtaccgcagcagcatccgagcggc
1

MetValGlnLeuGlyLysLeuLeuArgValLeuThrLeuMetLysPheProCysCysValLeuGluValLeuLeuCysValLeuAlaAlaAlaArgGlyGlnGluMet
atggtccagctggggaagctgctccgtccgatttgatgaagttccctgctgcgtgctggaggtactcctgtgcgtgctggcggccgcggccgcggccagagatg
                   20                                                      60

TyrAlaProHisSerIleArgIleGluGlyLeuGlyPheProValHisAlaLysGlyValProCysGlyAspIleLysArgGluAsnGlyIle
tacgccccgcactcgatccgatcgagggggacgtcaccccctgggggttcccagtgcacgccaaggtccctgcggcggtcccgcgacatcaagagaggagaatgggatc
                                            100

HisArgLeuGluAlaAlaMetLeuTyrAlaLeuAspSerAsnSerAspProAsnValThrLeuGlyAlaArgIleLeuAspThrCysSerArgAspThr
cacaggctggaagctatgctttatgccctggacagcaacagcgatcccaatgtcaccttaggcgcgcggatcctggacacttgttccagggacactttat
                                                                       140

AlaLeuGluSerLeuThrPheValGlnAlaLeuIleLeuGlnLysAspThrSerAspValPheValArgCysThrArgAsnGlyGluProProValPheValLysProGluLysValValGly
gcgctggaacagtgcttacttcgtccaggccttatccagaagaacacctcgacgtgcgttgcaccaacggagagccccggtttcgtcaagccagagaagtagttga
                                                             180

ValIleAlaSerGlySerSerMetValSerIleMetLeuArgLeuPheGlnIleProGlnIleSerTyrAlaSerThrAlaProGluLeuSerAspArgArg
gtgattgggctctcgggagctccgtctccatcatggtagccaacatctgaggctttcagatccccagattagtagtccgctccgaactcagtgatgaccggcgc
                                                           220

TyrAspPheSerArgValValProProAspSerPheGlnAlaGlnAlaMetValAspIleValLysAlaLeuGlyTrpAsnTyrValSerThrLeuAlaSerGluGlySer
tatgactttctctctctcgagtggccccgcctgattcctccaagcccagcgatggtgacatgtgaaaggcttgggctgaattacgtctactcttgcatctgaaggaagc
                                                     260

TyrGlyLysGlyValGluSerPheThrGlnIleSerLysGluValLeuCysIleAlaGlnSerValArgIleProGlnGluArgLysAspArgThrIleAspPhe
tatggagagaaagtgtgagcccttcacacagatttcaaagagagcaggtgctctgcattgccaagccagtccgtgagaatcccaaagagcaaagaggaccattgactt
                                        300

AspArgIleIleLeuLysGlnLeuLeuAspThrProAsnSerArgAlaValAlaIlePheAlaAsnAspAlaGluAspIleLeuGlnIleLeuLysGlnIleLeuLysGlnIleLeuLysGlnIleLeuLysGlnIleLeuLysGlnIleLeuLysGlnIleLeuLysGlnIleLeuGlnIleLeuLysGlnIleLeuArgAlaAlaAspGlnVal
gatagaattatcaaacagctcttgacactccaactccaggccgtgtgatttttgccaacgatgagagattaaagcagatcctgccgccgcaaaagagctgaccaagta
                                                                                      340

GlyHisPheLeuTrpValGlySerAspSerTrpGlySerLysIleAsnProLeuHisGlnHisGluAlaIleThrIleGlnProLysArgAlaThrValGlu
ggccatttcctggtgtcgggtcagacagctggggttccaaatcaaccactcagcaacgaagagccataacaatcagctaacagggcaacctggaa
                                                                                 380

GlyPheAspAlaTyrPheThrSerArgThrLeuGluAsnAsnArgAsnPheAlaGluTyrTrpPheAlaGluTyrTrpAlaAlaAspPheAlaAlaGluTyrTrpAsnPheAsnValCysLysLeuThrIleSerGlySer
ggatttgatgcttactttcacatcccggacacttgaaaaacaacaggagaaatgtgtttgcgaatactggaagaaaacttcaactcaagttgacaattagtgggtcc LysLysGluThrAspArgLysCysThrGlyGlnGluArgIleGlyLysAspSerAsnTyrGluGlnGluGlyLysValGlnPheValIleAspAlaValTyrAlaMetAla
aaaaagaagacacagatcgcaaatgcaccaggacaggagcgaattgaaaagactccaatatgagcaggaagtaagtacagtttgtttgattgatgtctatgccatggcc
420
HisAlaLeuHisHisMetAsnLysAspLeuCysAlaAspTyrArgGlyValCysProGluMetGluGlnAlaGlyGlyLysLeuLeuLysTyrIleArgHisValAsn
catgctcttcatcacatgaacaaggatctgtgtgctgactacccgcggagtgtgtgccagaggagatgagcaggcggcaagaagttgttgaagtatatccgccatgttaac
PheAsnGlySerAlaGlyThrProValMetPheAsnLysAsnGlyAspAlaProGlyArgTyrAspIlePheGlnTyrGlnThrThrAsnThrThrAsnProGlyTyrArg
ttcaatggtagtgctgaacccagtaatgtttaacaaaaatggcgatgtccagggcgttatgacatcttccaatacagacaacaacaacaacccctggtatcgt
500
LeuIleGlyGlnTrpThrAspGluLeuGlnLeuAsnIleGluAsnMetGlnTrpGlyLysGlyValArgGluIleProSerSerValCysThrLeuProCysLysProGlyGln
ctcattgggcagtggacagatgaacttcagtcaatatagagacaagcagtggggcaaaggagtccgagagatccatcctctgtgtacattgccatgcaagcctggcaa
540
ArgLysThrGlnLysGlyThrProCysCysTrpThrProCysThrCysGluProCysGlyTyrGlnPheAspGlyGlyTyrGlnPheAspGluMetThrCysGlnHisCysProTyrArgAspGlnArg
aggaagaagacacagaagggaacgccttgctgctgaccctgtgagccctgtgatgagtaccagtatcagttgatgagatgacctgcagcattgtcccctacgaccagagg
I
ProAsnGluAsnArgThrGlyCysGlnAsnIleProIleIleLysGluTrpHisSerProTrp AlaValIleProValPheLeuAlaMetLeuGlyIleIleAlaThrIlePhe
cccaatgagaactggctgtcagaacatcccaatcaaactgagtggcactcccccctggctgtcattcctgctgtctcctggacatgtgggatcattgcccaccatcttt
620
II
ValMetAlaThrPheIle ArgTyrAsnAspThrProIleValArgProIleValArgAlaSerGlyArgGlu LeuSerTyrValLeuLeuThrGlyIlePheLeuCysTyrIleIleThrGlyPheLeuMet
gtcatggcaactttcatccgctacaatgacacacacccattgcagggaactcagtcagggcatcgggggaactcagtcagcctatgtttattgacagcatcttctctgctatatcatcacctcctaatg
III
IleAla LysProAspValAlaValCysSerPheArgArg ValPheLeuGlyLeuGlyMetCysIleIleSerTyrAlaAlaLeuThrLysThrAsn ArgIleTyrArgIlePhe
attgccaaaccagatgtggcagtgtgcagtttccgacgtgtcttccgacgtgtcttcgggctgggcatgtgcatctcagtgcccttttaacaagagcaatcgattatcgcatattc
IV
GluGlnGlyLysLysSerValThrAlaProArgLeuIleSerProThrSerGln LeuAlaIleThrSerSerLeuIleSerValGlnLeuLeuGlyValPheIleTrpPheGly
gagcagggcaagaaatcggtgacagctccagactcccaagctcaacgtcgcgatcacttccagtttaatatggtgcagcttcagtgtcttcattggtttggg
700 740
Val AspProProAsnIleIleIleAspTyrAspHisLysThrMetAsnProGlyGluAlaArgGlyValLeuLysCysSerMetArgAsp LeuGlnIleIleCysSerSerLeu
gttgaccccccaacattatcatagactacgatcataagaccatgaacccaggagtgttccaaatgacatgagagaccttcaaatcatttgttccctg
780
V
GlyTyrSerIleLeuMetValThrCysThrValTyrAlaIle LysThrArgGlyValProGluAsnPheAsnGluAlaLys ProIleGlyPheThrMetTyrThrThrCysIle
ggatatagcattctccatggtcactgtactgtgtaccatcaagactgggtccatgaagcaaggccattggttcactatgtacacgacgtgtatc
VI

FIG. 1B

ValTrpLeuAlaPheIleProIlePhePheGly ThrAlaGlnSerAlaGluLysLeuTyrIleGlnThrThrThrLeu ThrIleSerMetAsnLeuSerAlaSerValAlaLeu
gtatggcttgccttcatcccaatattttggcacagcgcagtcagcagcgcagaaaagctactacacgcttacaatctcatgaactaagtgctcagtgcctg
VII
GlyMetLeuTyrMetProLysValTyrIleIleIlePhe HisProGluLeuAsnValGlnLysArgLysArgSerPheLysAlaValThrAlaAlaThrMetSerSerArg
ggaatgctatacatgcc gaaagtgtacatcatcatttt ccacctgaactcaatgtccagaaacggaagcgaagcttcaaggccgtcacagcagccacatgtcatcaagg
820                                     860

LeuSerHisLysPro
ctgtcacacaaaccc

SerAspArgProAsnGlyGluAlaLysThrGluLeuCysGluAsnSerProAlaAlaLysLysTyrValSerTyrAsnAsnLeuValIle
agtgacaggcccaacggtgaggcaaagacagaacctgtgaaaatgtagacccaaaacagcctgctgcaaaaaagaagtatgtcagttatcagttatataacctggttatctaacctgttccatgc
catggagccacagagaggagaagacctcagttattctgtcacccacggtggcattgactcttggtccgccgcttcctatctctggaggagcttcctcgtgcc
                   900                                              915

FIG. 1C

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2997 base pairs
      (B) TYPE: nucleic acid
      (C) STRANDEDNESS: single
      (D) TOPOLOGY: linear (ii) MOLECULE TYPE: cDNA (iii) FEATURE:
    (A) NAME/KEY: CDS
    (B) LOCATION: 133..2877

(iv) SEQUENCE DESCRIPTION: SEQ ID NO:1:

```
ACCCTCTGTG CCTACAGAAG TCCCTGGGCT TCCCCCAAAG GAGCTCACCT CCAGAAGCCC      60

GGACCTGGGA GAGCCCACCA GCATACCCTC CAGCGCCGCC GCCGCCGCTA CCGCAGCAGC     120

ATCCGGAGCG GC ATG GTC CAG CTG GGG AAG CTG CTC CGC GTC CTG ACT        168
              Met Val Gln Leu Gly Lys Leu Leu Arg Val Leu Thr
                1               5                  10

TTG ATG AAG TTC CCC TGC TGC GTG CTG GAG GTG CTC CTG TGC GTG CTG      216
Leu Met Lys Phe Pro Cys Cys Val Leu Glu Val Leu Leu Cys Val Leu
         15                  20                  25

GCG GCG GCG GCG CGC GGC CAG GAG ATG TAC GCC CCG CAC TCG ATC CGG      264
Ala Ala Ala Ala Arg Gly Gln Glu Met Tyr Ala Pro His Ser Ile Arg
 30                  35                  40

ATC GAG GGG GAC GTC ACC CTT GGG GGG TTG TTC CCA GTG CAC GCC AAG      312
Ile Glu Gly Asp Val Thr Leu Gly Gly Leu Phe Pro Val His Ala Lys
 45                  50                  55                  60

GGT CCC AGC GGA GTG CCC TGC GGC GAC ATC AAG AGG GAG AAT GGG ATC      360
Gly Pro Ser Gly Val Pro Cys Gly Asp Ile Lys Arg Glu Asn Gly Ile
             65                  70                  75

CAC AGG CTG GAA GCT ATG CTT TAT GCC CTG GAC CAG ATC AAC AGC GAT      408
His Arg Leu Glu Ala Met Leu Tyr Ala Leu Asp Gln Ile Asn Ser Asp
         80                  85                  90

CCC AAC CTG CTG CCC AAT GTA ACG TTA GGC GCG CGG ATC CTG GAC ACT      456
Pro Asn Leu Leu Pro Asn Val Thr Leu Gly Ala Arg Ile Leu Asp Thr
     95                 100                 105

TGT TCC AGG GAC ACT TAT GCG CTC GAA CAG TCG CTC ACT TTC GTC CAG      504
Cys Ser Arg Asp Thr Tyr Ala Leu Glu Gln Ser Leu Thr Phe Val Gln
110                 115                 120

GCG CTT ATC CAG AAG GAC ACC TCC GAC GTG CGT TGC ACC AAC GGA GAG      552
Ala Leu Ile Gln Lys Asp Thr Ser Asp Val Arg Cys Thr Asn Gly Glu
125                 130                 135                 140

CCC CCG GTT TTC GTC AAG CCA GAG AAA GTA GTT GGA GTG ATT GGG GCT      600
Pro Pro Val Phe Val Lys Pro Glu Lys Val Val Gly Val Ile Gly Ala
                145                 150                 155

TCG GGG AGC TCC GTC TCC ATC ATG GTA GCC AAC ATC TTG AGG CTT TTT      648
Ser Gly Ser Ser Val Ser Ile Met Val Ala Asn Ile Leu Arg Leu Phe
            160                 165                 170

CAG ATC CCT CAG ATT AGT TAT GCA TCC ACG GCT CCT GAA CTC AGT GAT      696
Gln Ile Pro Gln Ile Ser Tyr Ala Ser Thr Ala Pro Glu Leu Ser Asp
        175                 180                 185

GAC CGG CGC TAT GAC TTC TTC TCT CGA GTG GTC CCG CCT GAT TCC TTC      744
Asp Arg Arg Tyr Asp Phe Phe Ser Arg Val Val Pro Pro Asp Ser Phe
    190                 195                 200

CAA GCC CAG GCG ATG GTT GAC ATT GTA AAG GCT TTG GGC TGG AAT TAC      792
Gln Ala Gln Ala Met Val Asp Ile Val Lys Ala Leu Gly Trp Asn Tyr
205                 210                 215                 220

GTG TCT ACT CTT GCA TCT GAA GGA AGC TAT GGA GAG AAA GGT GTG GAG      840
Val Ser Thr Leu Ala Ser Glu Gly Ser Tyr Gly Glu Lys Gly Val Glu
                225                 230                 235

TCC TTC ACA CAG ATT TCC AAA GAG GCA GGT GGG CTC TGC ATT GCC CAG      888
Ser Phe Thr Gln Ile Ser Lys Glu Ala Gly Gly Leu Cys Ile Ala Gln
            240                 245                 250

TCC GTG AGA ATC CCC CAA GAG CGC AAA GAC AGG ACC ATT GAC TTT GAT      936
Ser Val Arg Ile Pro Gln Glu Arg Lys Asp Arg Thr Ile Asp Phe Asp
        255                 260                 265
```

-continued

| | |
|---|---|
| AGA ATT ATC AAA CAG CTC TTG GAC ACT CCC AAC TCC AGG GCC GTC GTG<br>Arg Ile Ile Lys Gln Leu Leu Asp Thr Pro Asn Ser Arg Ala Val Val<br>270              275              280 | 984 |
| ATT TTT GCC AAC GAT GAG GAT ATA AAG CAG ATC CTT GCC GCC GCC AAA<br>Ile Phe Ala Asn Asp Glu Asp Ile Lys Gln Ile Leu Ala Ala Ala Lys<br>285              290              295              300 | 1032 |
| AGA GCT GAC CAA GTA GGC CAT TTT CTC TGG GTC GGG TCA GAC AGC TGG<br>Arg Ala Asp Gln Val Gly His Phe Leu Trp Val Gly Ser Asp Ser Trp<br>305              310              315 | 1080 |
| GGT TCC AAA ATC AAC CCA CTG CAT CAG CAC GAA GAT ATT GCG GAA GGA<br>Gly Ser Lys Ile Asn Pro Leu His Gln His Glu Asp Ile Ala Glu Gly<br>320              325              330 | 1128 |
| GCC ATA ACA ATC CAG CCT AAA AGG GCA ACC GTG GAA GGA TTT GAT GCT<br>Ala Ile Thr Ile Gln Pro Lys Arg Ala Thr Val Glu Gly Phe Asp Ala<br>335              340              345 | 1176 |
| TAC TTC ACA TCC CGG ACA CTT GAA AAC AAC AGG AGA AAT GTA TGG TTT<br>Tyr Phe Thr Ser Arg Thr Leu Glu Asn Asn Arg Arg Asn Val Trp Phe<br>350              355              360 | 1224 |
| GCC GAA TAC TGG GAA GAA AAC TTC AAC TGC AAG TTG ACA ATT AGT GGG<br>Ala Glu Tyr Trp Glu Glu Asn Phe Asn Cys Lys Leu Thr Ile Ser Gly<br>365              370              375              380 | 1272 |
| TCC AAA AAA GAA GAC ACA GAT CGC AAA TGC ACA GGA CAG GAG CGA ATT<br>Ser Lys Lys Glu Asp Thr Asp Arg Lys Cys Thr Gly Gln Glu Arg Ile<br>385              390              395 | 1320 |
| GGA AAA GAC TCC AAT TAT GAG CAG GAA GGT AAA GTA CAG TTT GTG ATT<br>Gly Lys Asp Ser Asn Tyr Glu Gln Glu Gly Lys Val Gln Phe Val Ile<br>400              405              410 | 1368 |
| GAT GCT GTC TAT GCC ATG GCC CAT GCT CTT CAT CAC ATG AAC AAG GAT<br>Asp Ala Val Tyr Ala Met Ala His Ala Leu His His Met Asn Lys Asp<br>415              420              425 | 1416 |
| CTG TGT GCT GAC TAC CGC GGA GTG TGC CCA GAG ATG GAG CAA GCA GGC<br>Leu Cys Ala Asp Tyr Arg Gly Val Cys Pro Glu Met Glu Gln Ala Gly<br>430              435              440 | 1464 |
| GGC AAG AAG TTG TTG AAG TAT ATC CGC CAT GTT AAC TTC AAT GGT AGT<br>Gly Lys Lys Leu Leu Lys Tyr Ile Arg His Val Asn Phe Asn Gly Ser<br>445              450              455              460 | 1512 |
| GCT GGA ACC CCA GTA ATG TTT AAC AAA AAT GGC GAT GCT CCA GGG CGT<br>Ala Gly Thr Pro Val Met Phe Asn Lys Asn Gly Asp Ala Pro Gly Arg<br>465              470              475 | 1560 |
| TAT GAC ATC TTC CAA TAC CAG ACA ACA AAC ACA ACC AAC CCT GGT TAT<br>Tyr Asp Ile Phe Gln Tyr Gln Thr Thr Asn Thr Thr Asn Pro Gly Tyr<br>480              485              490 | 1608 |
| CGT CTC ATT GGG CAG TGG ACA GAT GAA CTT CAG CTC AAT ATA GAG GAC<br>Arg Leu Ile Gly Gln Trp Thr Asp Glu Leu Gln Leu Asn Ile Glu Asp<br>495              500              505 | 1656 |
| ATG CAG TGG GGC AAA GGA GTC CGA GAG ATC CCA TCC TCT GTG TGT ACA<br>Met Gln Trp Gly Lys Gly Val Arg Glu Ile Pro Ser Ser Val Cys Thr<br>510              515              520 | 1704 |
| TTG CCA TGC AAG CCT GGG CAA AGG AAG AAG ACA CAG AAG GGA ACG CCT<br>Leu Pro Cys Lys Pro Gly Gln Arg Lys Lys Thr Gln Lys Gly Thr Pro<br>525              530              535              540 | 1752 |
| TGC TGC TGG ACC TGT GAG CCC TGT GAT GGA TAC CAG TAT CAG TTT GAT<br>Cys Cys Trp Thr Cys Glu Pro Cys Asp Gly Tyr Gln Tyr Gln Phe Asp<br>545              550              555 | 1800 |
| GAG ATG ACC TGT CAG CAT TGT CCC TAC GAC CAG AGG CCC AAT GAG AAC<br>Glu Met Thr Cys Gln His Cys Pro Tyr Asp Gln Arg Pro Asn Glu Asn<br>560              565              570 | 1848 |
| CGA ACT GGC TGT CAG AAC ATC CCA ATC ATC AAA CTG GAG TGG CAC TCC<br>Arg Thr Gly Cys Gln Asn Ile Pro Ile Ile Lys Leu Glu Trp His Ser<br>575              580              585 | 1896 |

```
CCC TGG GCT GTC ATT CCT GTC TTC CTG GCA ATG TTG GGG ATC ATT GCC    1944
Pro Trp Ala Val Ile Pro Val Phe Leu Ala Met Leu Gly Ile Ile Ala
590                 595                 600

ACC ATC TTT GTC ATG GCA ACT TTC ATC CGC TAC AAT GAC ACA CCC ATT    1992
Thr Ile Phe Val Met Ala Thr Phe Ile Arg Tyr Asn Asp Thr Pro Ile
605                 610                 615                 620

GTC AGG GCA TCT GGG CGG GAA CTC AGC TAT GTT TTA TTG ACA GGC ATC    2040
Val Arg Ala Ser Gly Arg Glu Leu Ser Tyr Val Leu Leu Thr Gly Ile
                625                 630                 635

TTT CTC TGC TAT ATC ATC ACC TTC CTA ATG ATT GCC AAA CCA GAT GTG    2088
Phe Leu Cys Tyr Ile Ile Thr Phe Leu Met Ile Ala Lys Pro Asp Val
            640                 645                 650

GCA GTG TGT TCT TTC CGA CGT GTC TTC TTG GGC TTG GGC ATG TGT ATT    2136
Ala Val Cys Ser Phe Arg Arg Val Phe Leu Gly Leu Gly Met Cys Ile
        655                 660                 665

AGT TAT GCT GCC CTT TTA ACA AAG ACC AAT CGG ATT TAT CGC ATA TTC    2184
Ser Tyr Ala Ala Leu Leu Thr Lys Thr Asn Arg Ile Tyr Arg Ile Phe
670                 675                 680

GAG CAG GGC AAG AAA TCG GTG ACA GCT CCC AGA CTC ATA AGC CCA ACG    2232
Glu Gln Gly Lys Lys Ser Val Thr Ala Pro Arg Leu Ile Ser Pro Thr
685                 690                 695                 700

TCA CAA CTG GCG ATC ACT TCC AGT TTA ATA TCG GTG CAG CTT CTA GGT    2280
Ser Gln Leu Ala Ile Thr Ser Ser Leu Ile Ser Val Gln Leu Leu Gly
                705                 710                 715

GTC TTC ATT TGG TTT GGG GTT GAC CCC CCC AAC ATT ATC ATA GAC TAC    2328
Val Phe Ile Trp Phe Gly Val Asp Pro Pro Asn Ile Ile Ile Asp Tyr
            720                 725                 730

GAT GAG CAT AAG ACC ATG AAC CCA GAA CAA GCA AGG GGT GTT CTC AAA    2376
Asp Glu His Lys Thr Met Asn Pro Glu Gln Ala Arg Gly Val Leu Lys
        735                 740                 745

TGT GAC ATC ACA GAC CTT CAA ATC ATT TGT TCC CTG GGA TAT AGC ATT    2424
Cys Asp Ile Thr Asp Leu Gln Ile Ile Cys Ser Leu Gly Tyr Ser Ile
750                 755                 760

CTT CTC ATG GTC ACA TGT ACT GTG TAT GCC ATC AAG ACT CGG GGC GTA    2472
Leu Leu Met Val Thr Cys Thr Val Tyr Ala Ile Lys Thr Arg Gly Val
765                 770                 775                 780

CCA GAG AAT TTT AAT GAA GCC AAG CCC ATT GGG TTC ACT ATG TAC ACG    2520
Pro Glu Asn Phe Asn Glu Ala Lys Pro Ile Gly Phe Thr Met Tyr Thr
                785                 790                 795

ACG TGT ATC GTA TGG CTT GCC TTC ATC CCA ATA TTT TTT GGC ACA GCG    2568
Thr Cys Ile Val Trp Leu Ala Phe Ile Pro Ile Phe Phe Gly Thr Ala
            800                 805                 810

CAG TCA GCA GAA AAG CTC TAC ATA CAA ACT ACC ACG CTT ACA ATC TCC    2616
Gln Ser Ala Glu Lys Leu Tyr Ile Gln Thr Thr Thr Leu Thr Ile Ser
        815                 820                 825

ATG AAC CTA AGT GCG TCA GTG GCG CTG GGA ATG CTA TAC ATG CCG AAA    2664
Met Asn Leu Ser Ala Ser Val Ala Leu Gly Met Leu Tyr Met Pro Lys
830                 835                 840

GTG TAC ATC ATC ATT TTC CAC CCT GAA CTC AAT GTC CAG AAA CGG AAG    2712
Val Tyr Ile Ile Ile Phe His Pro Glu Leu Asn Val Gln Lys Arg Lys
845                 850                 855                 860

CGA AGC TTC AAG GCC GTA GTC ACA GCA GCC ACC ATG TCA TCA AGG CTG    2760
Arg Ser Phe Lys Ala Val Val Thr Ala Ala Thr Met Ser Ser Arg Leu
                865                 870                 875

TCA CAC AAA CCC AGT GAC AGG CCC AAC GGT GAG GCA AAG ACA GAA CTC    2808
Ser His Lys Pro Ser Asp Arg Pro Asn Gly Glu Ala Lys Thr Glu Leu
            880                 885                 890

TGT GAA AAT GTA GAC CCA AAC AGC CCT GCT GCA AAA AAG AAG TAT GTC    2856
Cys Glu Asn Val Asp Pro Asn Ser Pro Ala Ala Lys Lys Lys Tyr Val
        895                 900                 905
```

-continued

```
AGT TAT AAT AAC CTG GTT ATC TAACCTGTTC CATGCCATGG AGCCACAGAG    2907
Ser Tyr Asn Asn Leu Val Ile
    910             915

GAGGAAGACC TTCAGTTATT CTGTCACCCA CGGTGGCATT GGACTCTTGG TCCTGCCCGC   2967

TTCCTATCTC TGGAGGAGCT TCCTCGTGCC                                    2997
```

(2) INFORMATION FOR SEQ ID NO:2:

(i) SEQUENCE CHARACTERISTICS:
        (A) LENGTH: 915 amino acids
        (B) TYPE: amino acid
        (D) TOPOLOGY: linear (ii) MOLECULE TYPE: protein (iii) SEQUENCE DESCRIPTION: SEQ ID NO:2:

```
Met Val Gln Leu Gly Lys Leu Leu Arg Val Leu Thr Leu Met Lys Phe
 1               5                  10                  15

Pro Cys Cys Val Leu Glu Val Leu Leu Cys Val Leu Ala Ala Ala Ala
                20                  25                  30

Arg Gly Gln Glu Met Tyr Ala Pro His Ser Ile Arg Ile Glu Gly Asp
            35                  40                  45

Val Thr Leu Gly Gly Leu Phe Pro Val His Ala Lys Gly Pro Ser Gly
        50                  55                  60

Val Pro Cys Gly Asp Ile Lys Arg Glu Asn Gly Ile His Arg Leu Glu
 65                  70                  75                  80

Ala Met Leu Tyr Ala Leu Asp Gln Ile Asn Ser Asp Pro Asn Leu Leu
                85                  90                  95

Pro Asn Val Thr Leu Gly Ala Arg Ile Leu Asp Thr Cys Ser Arg Asp
            100                 105                 110

Thr Tyr Ala Leu Glu Gln Ser Leu Thr Phe Val Gln Ala Leu Ile Gln
        115                 120                 125

Lys Asp Thr Ser Asp Val Arg Cys Thr Asn Gly Glu Pro Pro Val Phe
130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu Ser Asp Asp Arg Arg Tyr
            180                 185                 190

Asp Phe Phe Ser Arg Val Val Pro Pro Asp Ser Phe Gln Ala Gln Ala
        195                 200                 205

Met Val Asp Ile Val Lys Ala Leu Gly Trp Asn Tyr Val Ser Thr Leu
    210                 215                 220

Ala Ser Glu Gly Ser Tyr Gly Glu Lys Gly Val Glu Ser Phe Thr Gln
225                 230                 235                 240

Ile Ser Lys Glu Ala Gly Gly Leu Cys Ile Ala Gln Ser Val Arg Ile
                245                 250                 255

Pro Gln Glu Arg Lys Asp Arg Thr Ile Asp Phe Asp Arg Ile Ile Lys
            260                 265                 270

Gln Leu Leu Asp Thr Pro Asn Ser Arg Ala Val Ile Phe Ala Asn
        275                 280                 285

Asp Glu Asp Ile Lys Gln Ile Leu Ala Ala Ala Lys Arg Ala Asp Gln
    290                 295                 300

Val Gly His Phe Leu Trp Val Gly Ser Asp Ser Trp Gly Ser Lys Ile
305                 310                 315                 320
```

-continued

```
Asn Pro Leu His Gln His Glu Asp Ile Ala Glu Gly Ala Ile Thr Ile
            325                 330                 335

Gln Pro Lys Arg Ala Thr Val Glu Gly Phe Asp Ala Tyr Phe Thr Ser
            340                 345                 350

Arg Thr Leu Glu Asn Asn Arg Asn Val Trp Phe Ala Glu Tyr Trp
            355                 360                 365

Glu Glu Asn Phe Asn Cys Lys Leu Thr Ile Ser Gly Ser Lys Lys Glu
    370                 375                 380

Asp Thr Asp Arg Lys Cys Thr Gly Gln Glu Arg Ile Gly Lys Asp Ser
385                 390                 395                 400

Asn Tyr Glu Gln Glu Gly Lys Val Gln Phe Val Ile Asp Ala Val Tyr
            405                 410                 415

Ala Met Ala His Ala Leu His His Met Asn Lys Asp Leu Cys Ala Asp
            420                 425                 430

Tyr Arg Gly Val Cys Pro Glu Met Glu Gln Ala Gly Gly Lys Lys Leu
            435                 440                 445

Leu Lys Tyr Ile Arg His Val Asn Phe Asn Gly Ser Ala Gly Thr Pro
    450                 455                 460

Val Met Phe Asn Lys Asn Gly Asp Ala Pro Gly Arg Tyr Asp Ile Phe
465                 470                 475                 480

Gln Tyr Gln Thr Thr Asn Thr Thr Asn Pro Gly Tyr Arg Leu Ile Gly
            485                 490                 495

Gln Trp Thr Asp Glu Leu Gln Leu Asn Ile Glu Asp Met Gln Trp Gly
            500                 505                 510

Lys Gly Val Arg Glu Ile Pro Ser Ser Val Cys Thr Leu Pro Cys Lys
            515                 520                 525

Pro Gly Gln Arg Lys Lys Thr Gln Lys Gly Thr Pro Cys Cys Trp Thr
            530                 535                 540

Cys Glu Pro Cys Asp Gly Tyr Gln Tyr Gln Phe Asp Glu Met Thr Cys
545                 550                 555                 560

Gln His Cys Pro Tyr Asp Gln Arg Pro Asn Glu Asn Arg Thr Gly Cys
            565                 570                 575

Gln Asn Ile Pro Ile Ile Lys Leu Glu Trp His Ser Pro Trp Ala Val
            580                 585                 590

Ile Pro Val Phe Leu Ala Met Leu Gly Ile Ile Ala Thr Ile Phe Val
            595                 600                 605

Met Ala Thr Phe Ile Arg Tyr Asn Asp Thr Pro Ile Val Arg Ala Ser
            610                 615                 620

Gly Arg Glu Leu Ser Tyr Val Leu Leu Thr Gly Ile Phe Leu Cys Tyr
625                 630                 635                 640

Ile Ile Thr Phe Leu Met Ile Ala Lys Pro Asp Val Ala Val Cys Ser
            645                 650                 655

Phe Arg Arg Val Phe Leu Gly Leu Gly Met Cys Ile Ser Tyr Ala Ala
            660                 665                 670

Leu Leu Thr Lys Thr Asn Arg Ile Tyr Arg Ile Phe Glu Gln Gly Lys
            675                 680                 685

Lys Ser Val Thr Ala Pro Arg Leu Ile Ser Pro Thr Ser Gln Leu Ala
            690                 695                 700

Ile Thr Ser Ser Leu Ile Ser Val Gln Leu Leu Gly Val Phe Ile Trp
705                 710                 715                 720

Phe Gly Val Asp Pro Pro Asn Ile Ile Ile Asp Tyr Asp Glu His Lys
            725                 730                 735
```

```
Thr Met Asn Pro Glu Gln Ala Arg Gly Val Leu Lys Cys Asp Ile Thr
            740                 745                 750

Asp Leu Gln Ile Ile Cys Ser Leu Gly Tyr Ser Ile Leu Leu Met Val
            755                 760                 765

Thr Cys Thr Val Tyr Ala Ile Lys Thr Arg Gly Val Pro Glu Asn Phe
            770                 775                 780

Asn Glu Ala Lys Pro Ile Gly Phe Thr Met Tyr Thr Thr Cys Ile Val
785                 790                 795                 800

Trp Leu Ala Phe Ile Pro Ile Phe Phe Gly Thr Ala Gln Ser Ala Glu
                805                 810                 815

Lys Leu Tyr Ile Gln Thr Thr Thr Leu Thr Ile Ser Met Asn Leu Ser
            820                 825                 830

Ala Ser Val Ala Leu Gly Met Leu Tyr Met Pro Lys Val Tyr Ile Ile
            835                 840                 845

Ile Phe His Pro Glu Leu Asn Val Gln Lys Arg Lys Arg Ser Phe Lys
            850                 855                 860

Ala Val Val Thr Ala Ala Thr Met Ser Ser Arg Leu Ser His Lys Pro
865                 870                 875                 880

Ser Asp Arg Pro Asn Gly Glu Ala Lys Thr Glu Leu Cys Glu Asn Val
                885                 890                 895

Asp Pro Asn Ser Pro Ala Ala Lys Lys Lys Tyr Val Ser Tyr Asn Asn
            900                 905                 910

Leu Val Ile
        915

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) SEQUENCE DESCRIPTION: SEQ ID NO:3:

Val Asp Pro Asn Ser Pro Ala Ala Lys Lys Lys Tyr Val Ser
            5                   10

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:4:

GCTCAGGGTC AGATACTTTC TCTTTCAGGT GTCAG                            35

(2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear
```

-continued

```
    (ii) MOLECULE TYPE: cDNA (iii) SEQUENCE DESCRIPTION: SEQ ID NO:5:

ATTCAGGTAG CTTTTCAGGC CTTCAGTTAG AA                                        32
```

L-AP4 SENSITIVE GLUTAMATE RECEPTORS

GOVERNMENT SUPPORT

This invention was made in part by research grants received from the National Institutes of Health. The U.S. government may have certain rights in the invention.

BACKGROUND OF THE INVENTION

Glutamate is a major excitatory neurotransmitter in the mammalian central nervous system. The neurotransmitter activity of glutamate is primarily mediated by ligand-gated ion channels. The observation that glutamate also induces responses mediated by second messengers has led to the discovery of a distinct group of glutamate receptors coupled to G proteins, termed metabotropic receptors (mGluRs). Schoepp and Conn, *Trends Pharmacol. Sci.* 14: 13–20 (1993). The first described action of the glutamate metabotropic receptors was inositol phospholipid (PI) hydrolysis. Nicoletti et al., *J. Neurochem.* 46: 40–46 (1986) and Sugiyama et al., *Nature* 325: 531–533 (1987). Molecular cloning techniques have revealed a large family of metabotropic receptors with distinct transduction mechanisms, patterns of expression and sensitivities to glutamate agonists. Schoepp and Conn, supra.

Consistent with the molecular heterogeneity observed for the metabotropic receptors, electrophysiological studies have suggested diverse roles for these receptors in synaptic plasticity, presynaptic inhibition and regulation of cell excitability by ion channel modulation. Bashir et al., *Nature* 363: 347–363 (1993); Linden et al., *Neuron* 7: 81–89 (1991); Baskys and Malenka, *J. Physiol. (Lond.)* 444: 687–701 (1991); Charpak et al. *Nature* 347: 765–767 (1990); and Lester and Jahr, *Neuron* 5: 741–749 (1990). However, the specific mGluR receptors mediating these cellular functions are largely undefined.

Evidence for a physiological role for specific mGluR subtypes has been derived from work with selective agonists and antagonists of the receptors. For example, (1S,3R)-1-aminocyclopentane-1,3-dicarboxylic acid (ACPD) is a selective and potent activator of the mGluR1, mGluR2, mGluR3 and mGluR5 receptors. Masu et al., *Nature* 349: 760–765 (1991); Abe et al., *J. Biol. Chem.* 267: 13361–13368 (1992); Tanabe et al., Neuron 8: 169–179 (1992); and Tanabe et al., *J. Neurosci.* 13: 1372–1378 (1993). L-2-amino-4-phosphonobutryic acid (L-AP4) has been shown to activate mGluR4 and mGluR6. Id., Thomsen et al.,. *Eur. J. Pharmacol.* 227: 361–362 (1992); Nakajima et al., *J. Biol. Chem.* 268: 11868–11873 (1993). L-AP4 inhibits transmitter release and voltage-dependent calcium entry in selected brain and spinal cord neurons. Koerner and Cotman, *Brain Res.* 216: 192–198 (1981); Trombley and Westbrook, *J. Neurosci.* 12: 2-43-2050 (1992); and Sahara and Westbrook, *J. Neurosci.* 13: 3041–3050 (1993). But in retinal bipolar neurons, postsynaptic L-AP4 receptors activate a phosphodiesterase. Nawy and Jahr, *Nature* 346: 269–271 (1990).

Multiple mGluR subtypes can be present within the same group of neurons. As the cellular and subcellular localization of specific mGluRs may be important in shaping incoming sensory information, it is important to identify other receptors of the mGluR group. Once identified, specific agonists and antagonists can be prepared to modulate the responses associated with the receptor. Quite surprisingly, the present invention identifies a L-AP4 sensitive receptor that modulates transmitter release in neurons that express neither mGluR4 nor mGluR6, and fulfills other related needs.

SUMMARY OF THE INVENTION

The present invention provides novel isolated and purified metabotropic mGluR proteins referred to as mGluR7. The proteins may bind glutamate and induce cytoplasmic signal transduction. Allelic variants and mutations of mGluR7 proteins are included.

Also provided are isolated polynucleotides encoding mGluR7 and probes to the polynucleotides. The polynucleotides may be present in expression cassettes of the present invention that are useful for cellular transformation. Such transformed cell lines are also provided by the present invention. Transformed cells may be employed in methods for identifying compounds that alter mGluR7 metabolism.

Antibodies to mGluR7 receptor proteins are also provided by the present invention. The antibodies may be polyclonal or monoclonal. The antibodies may be employed to detect the presence of mGluR7 in biological samples, such as tissue homogenates, biological fluids, or cell surfaces.

BRIEF DESCRIPTION OF THE DRAWINGS

FIG. 1 shows the nucleotide sequence (SEQ ID NO:1) of a mGluR7 cDNA and the deduced amino acid sequence encoded thereby. The complete nucleotide sequence of a representative mGluR7 cDNA contains an open reading frame of 2745 bp and a translation initiation consensus sequence that surrounds the presumed initiator methionine. The solid line indicates the predicted signal peptide. The deduced amino acid sequence is 915 amino acids. The seven transmembrane segments (I–VII) were assigned based on hydrophobicity analysis. Asterisks mark putative N-glycosylation sites while a putative CaM kinase II phosphorylation site is indicated by a filled circle.

DESCRIPTION OF THE SPECIFIC EMBODIMENTS

Figure 2:
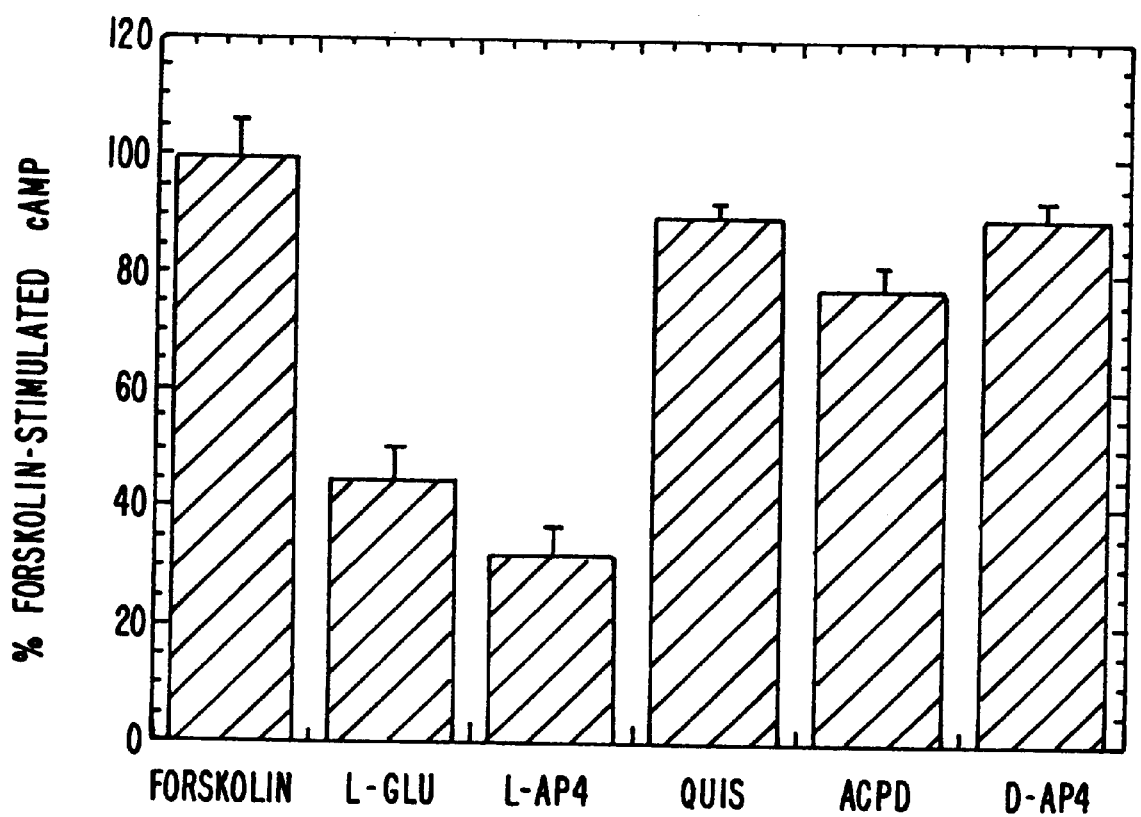
FIG. 2 depicts the inhibition of forskolin-stimulated cAMP production by mGluR7 in baby hamster kidney cells. BHK cells transfected with mGluR7 were preincubated for 20 minutes in IBMX (1 mM), then incubated for 10 minutes with forskolin (10 $\mu$M) in the presence or absence of agonists or antagonists. L-AP4 (1 mM) produced the largest inhibition while glutamate (1 mM), quisqualate (0.5 mM) and ACPD (1 mM) were less efficient. L-AP3 (1 mM) or MCPG (1 mM) did not antagonize the inhibition produced by L-AP4.

The present invention provides an isolated and purified protein receptor, designated "mGluR7," which is a member of the family of G protein coupled membrane receptors for the neurotransmitter glutamate. mGluR7 participates in the regulation of neurons, including neuroendocrine neurons, and particularly mitral/tufted neurons of the olfactory bulb. mGluR7 acts possibly by mediating inhibition of transmitter release at selected glutamatergic synapses. mGluR7 has an expression pattern in the central nervous system (CNS) distinct from other metabotropic receptors. The mGluR7 receptor can be coexpressed with other receptors of the mGluR family in single neurons, and thus the cellular effects of mGluR activation may result from the integrated action of several receptor subtypes that include mGluR7. Consequently, agonists and antagonists of the mGluR7-ligand interaction and mGluR7-mediated metabolism are important in regulating mGluR7-mediated neurotransmitter release. Isolated polynucleotides, including the cDNA which encodes mGluR7, are also described as part of the present invention, thereby providing means to conveniently produce isolated mGluR7 protein and to identify agonists and antagonists of the mGluR7-ligand interaction and mGluR7-mediated metabolism.

The isolated mGluR7 is meant to refer to mGluR7 which is found in a condition other than its native environment, such as apart from a neuron of the CNS. This includes, for example, substantially pure mGluR7 as defined below. More generally, isolated is meant to include mGluR7 as a heterologous component of a cell or other system. For example, mGluR7 may be expressed by a cell transfected with a DNA construct which encodes mGluR7 and which expresses other selected receptors or second messenger components. In another example described below, mGluR7 is expressed by a non-neuronal cell which has been co-transfected with a gene encoding mGluR4 receptor. Thus, in this context, the environment of isolated mGluR7 is not as it occurs in its native state, particularly when it is present in a system as an exogenous component.

mGluR7 is meant to include any protein either derived from a naturally occurring mGluR7, or which shares significant structural and functional characteristics peculiar to a naturally occurring mGluR7. Such a receptor may result when regions of a naturally occurring receptor are deleted or replaced in such a manner as to yield a protein having a similar function. Generally, it is desirable to conserve amino acid sequences associated with ligand binding. Conserved amino acids associated with the ligand-binding region of mGluR7 may include amino acids 72, 157–163, 180–184, 197, 410, and 472 of FIG. 1 (SEQ ID NO:1). mGluR7 transmembrane domains, which may include amino acid segments I–VII of FIG. 1, typically are more tolerant of amino acid mutations than N-terminal (extracellular) or C-terminal (cytoplasmic) domains. Preferred substitutions, especially in transmembrane domains, include, e.g., conservative amino acid substitutions and substitutions of amino acids from corresponding positions in other receptor molecules having seven transmembrane segments, particularly other mGluRs.

Homologous sequences, allelic variations, and natural mutants; induced point, deletion, and insertion mutants; alternatively expressed variants; proteins encoded by DNA which hybridize under high stringency conditions to nucleic acids which encode naturally occurring mGluR7; proteins retrieved from naturally occurring materials; and closely related proteins retrieved by antisera specific for mGluR7 proteins or peptides are also included. By "homologous" is meant sequences that have at least about 85% homology, preferably at least 90% homology, and more preferably at least about 95% or more homology to the amino acid sequence of a naturally occurring mGluR7 and retains the ability to bind glutamate or transduce intracellular signals.

With the mGluR7 and cDNA clones thereof provided herein, nucleotide and amino acid sequences may be determined by conventional means. See generally, Sambrook et al., *Molecular Cloning, A Laboratory Manual*, 2d ed., Cold Spring Harbor Laboratory Press, Cold Spring Harbor, NY, 1989, incorporated by reference herein. The invention provides isolated and cloned mGluR7 coding sequences which are capable of expressing the mGluR7 protein. By "isolated," it is meant that the molecules are removed from their natural genetic milieu. Thus, the invention provides mGluR7-encoding DNA molecules free of other genes with which they are ordinarily associated. In particular, the molecules are free of extraneous or unwanted coding sequences, and in a form suitable for use within genetically engineered protein production systems. A representative mGluR7-encoding cDNA is shown in SEQ ID NO:1.

Those skilled in the art will recognize that equivalent sequences could be prepared by substituting alternative codons. The present invention includes these equivalent sequences, as well as additional sequences that specifically hybridize to naturally occurring or equivalent sequences. Such additional sequences will hybridize to SEQ ID NO:1, or equivalents thereof, under conditions of high moderate stringency, i.e., conditions that differentiate related molecules from background. Those skilled in the art will recognize that lower stringent conditions serve to identify sequences encoding functionally equivalent polypeptides having common structural features (e.g., allelic variations). For example, conditions of moderate stringency for probes of 100 or more are prewashing in a solution of 5 X SSC, 0.5% SDS, 1.0 mM EDTA (pH 8.0) and hybridization conditions of 50° C. in 5 X SSC overnight (Sambrook et al., supra, previously incorporated herein by reference). Conditions of higher stringency may be utilized by increasing temperature or decreasing the salt concentration of the hybridization solution. Determination of stringency hybridization conditions is within the level of ordinary skill in the art.

Genomic or cDNA sequences encoding mGluR7 and homologous receptors of this subfamily of GluGR receptors can be obtained from libraries prepared from other species according to well known procedures. Complementary DNA encoding mGluR7 may be obtained by constructing a cDNA library from mRNA from, for example, olfactory bulb tissue. The library may be screened by transcribing the library and screening the clones with a complementary labeled oligonucleotide probe prepared in accordance with the mGluR7 nucleotide sequences set forth herein. As will be recognized by those skilled in the art, the rat mGluR7 sequence disclosed herein is a useful tool for cloning corresponding polynucleotides from other species. For instance, using oligonucleotide probes prepared from rodent mGluR7, such as whole length cDNA or shorter probes of at least about fourteen nucleotides to twenty-five or more nucleotides in length, and often as many as 40 to 50 nucleotides, prepared from areas of cDNA sequences specific for mGluR7 when compared to other known members of the mGluGR family, the mGluR7 of other species, such as lagomorph, avian, bovine, porcine, human, etc. may be obtained. Mammalian, especially primate, mGluR7 are of particular interest. If partial clones are obtained, it is necessary to join them in proper reading frame to produce a full length clone, using such techniques as endonuclease cleavage, ligation and loopout mutagenesis. It will be understood that the present invention includes degenerate polynucleotide sequences encoding amino acid sequences as described above.

A DNA sequence encoding mGluR7 is inserted into a suitable expression vector, which in turn is used to transfect eukaryotic cells for expression of mGluR7 or specific fragments thereof. Expression vectors for use in carrying out the present invention will comprise a promoter capable of directing the transcription of a cloned DNA and a transcriptional terminator. Depending on the host cell chosen, expression vectors may contain additional elements, such as one or more origins of replication, one or more selectable markers, enhancers, etc. Expression vector design is within the level of ordinary skill in the art. Expression vectors are also available from commercial suppliers.

To direct mGluR7 proteins of the present invention for transport to the plasma membrane, at least one signal sequence is operably linked to the DNA sequence of interest. The signal sequence may be derived from the mGluR7 coding sequence, from other signal sequences described in the art, or synthesized de novo.

Host cells for use in practicing the present invention include mammalian, avian, plant, insect and fungal cells, but preferably mammalian cells. Fungal cells, including species of yeast (e.g., Saccharomyces spp., particularly *S. cerevisiae*, Schizosaccharomyces spp.) or filamentous fungi (e.g., Aspergillus spp., Neurospora spp.) may be used as host cells within the present invention. Suitable yeast vectors for use in the present invention include YRp7 (Struhl et al., *Proc. Natl. Acad. Sci. USA* 76: 1035–1039, 1978), YEp13 (Broach et al., *Gene* 8: 121–133, 1979), POT vectors (Kawasaki et al, U.S. Pat. No. 4,931,373, which is incorporated by reference herein), pJDB249 and pJDB219 (Beggs, *Nature* 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources. Additional vectors, promoters and terminators for use in expressing the receptor of the invention in yeast are well known in the art and are reviewed by, for example, Emr, *Meth. Enzymol.* 185:231–279, (1990), incorporated herein by reference.

A variety of higher eukaryotic cells may serve as host cells for expression of the mGluR7, although not all cell lines will be capable of functional coupling of the receptor to the cell's second messenger systems. Cultured mammalian cells, such as BHK, CHO, Y1 (Shapiro et al., *TIPS Suppl.* 43–46 (1989)), NG108-15 (Dawson et al., *Neuroscience Approached Through Cell Culture*, Vol. 2, pages 89–114 (1989)), N1E-115 (Liles et al., *J. Biol. Chem.* 261:5307–5313 (1986)), PC 12 and COS-1 (ATCC CRL 1650) are preferred. Preferred BHK cell lines are the tk⁻ts13 BHK cell line (Waechter and Baserga, *Proc. Natl. Acad. Sci.* USA 79:1106–1110 (1982)) and the BHK 570 cell line (deposited with the American Type Culture Collection, 12301 Parklawn Dr., Rockville, MD, under accession number CRL 10314). A tk⁻ BHK cell line is available from the ATCC under accession number CRL 1632.

Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41: 521–530, 1985) and the SV40 promoter (Subramani et al., *Mol. Cell. Biol.* 1: 854–864, 1981). Cellular promoters include the mouse metallothionein-1 promoter (Palmiter et al., U.S. Pat. No. 4,579,821), a mouse $V_\kappa$ promoter (Bergman et al., *Proc. Natl. Acad. Sci.* USA 81: 7041–7045, 1983; Grant et al., *Nuc. Acids Res.* 15: 5496, 1987), a mouse $V_H$ promoter (Loh et al., *Cell* 33: 85–93, 1983) and the major late promoter from adenovirus 2 (Kaufman and Sharp, *Mol. Cell. Biol.* 2: 1304–13199, 1982). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (DeNoto et al., *Nuc. Acids Res.* 9: 3719–3730, 1981). The expression vectors may include a noncoding viral leader sequence, such as the adenovirus 2 tripartite leader, located between the promoter and the RNA splice sites. Vectors may also include enhancer sequences, such as the SV40 enhancer and the mouse $\mu$ enhancer (Gillies, *Cell* 33: 717–728, 1983). Expression vectors may also include sequences encoding the adenovirus VA RNAs.

Cloned DNA sequences may be introduced into cultured mammalian cells by, for example, calcium phosphate-mediated transfection (Wigler et al., *Cell* 14: 725, 1978; Corsaro and Pearson, *Somatic Cell Genetics* 7: 603, 1981; Graham and Van der Eb, *Virology* 52: 456, 1973.) Other techniques for introducing cloned DNA sequences into mammalian cells, such as electroporation (Neumann et al., *EMBO J.* 1: 841–845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene.

Selectable markers may be introduced into the cell on a separate plasmid at the same time as the mGluR7 gene of interest, or they may be introduced on the same plasmid. If on the same plasmid, the selectable marker and the mGluR7 gene can be under the control of different promoters or the same promoter, the latter arrangement producing a dicistronic message. Constructs of this type are known in the art (for example, Levinson and Simonsen, U.S. Pat. No. 4,713, 339). It may also be advantageous to add additional DNA, known as "carrier DNA" to the mixture which is introduced into the cells.

Transfected mammalian cells are allowed to grow for a period of time, typically 1–2 days, to begin expressing the mGluR7 DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Promoters, terminators and methods suitable for introducing expression vectors encoding recombinant mGluR7 into plant, avian and insect cells are widely available. The use of baculoviruses, for example, as vectors for expressing heterologous DNA sequences in insect cells has been reviewed by Atkinson et al. (*Pestic. Sci.* 28: 215–224, 1990). The use of *Agrobacterium rhizogenes* as vectors for expressing genes in plant cells has been reviewed by Sinkar et al. (*J. Biosci.* (*Banglaore*) 11: 47–58, 1987).

Host cells containing DNA constructs of the present invention are then cultured to produce recombinant mGluR7. The cells are cultured according to accepted methods in a culture medium containing nutrients required for growth of mammalian or other host cells. The growth medium will generally select for cells containing the DNA construct by, for example, drug selection or deficiency in an essential nutrient which is complemented by the selectable marker on the DNA construct or co-transfected with the DNA construct.

The mGluR7 produced according to the present invention may be purified from the recombinant expression systems or other sources using purification protocols that employ techniques generally available to those skilled in the art. The most convenient sources for obtaining large quantities of mGluR7 are cells which express the recombinant receptor protein. However, other sources, such as tissues, particularly tissues of the thalamus, neocortex and hypothalamus which contain the highest levels of mGluR7, may also be employed.

Purification of mGluR7 can be achieved by conventional chemical purification means, such as liquid chromatography, lectin affinity chromatography, gradient centrifugation, and gel electrophoresis, among others. Methods of protein purification are known in the art (see generally, Scopes, R., *Protein Purification*, Springer-Verlag, N.Y. (1982), which is incorporated herein by reference) and may be applied to the purification of the mGluR7 and particularly the recombinantly produced mGluR7 described herein. In a preferred embodiment immunoaffinity chromatography is employed using antibodies directed against mGluR7 as herein described. In another method of purification, the isolated polynucleotide encoding mGluR7 or portions thereof can be modified at the coding region for the amino terminus, just behind a signal sequence, with a sequence coding for a small hydrophilic peptide, such as described in U.S. Pat. Nos. 4,703,004 and 4,782,137, which are incorporated herein by reference. Specific antibodies for the peptide facilitate rapid purification of mGluR7, and the short peptide can then be removed with enterokinase.

Thus, as discussed above, the present invention provides mGluR7 isolated from its natural cellular environment, substantially free of other G protein coupled glutamate receptors. However, mGluR7 of the invention produced by recombinant techniques can be coexpressed with other mGluR receptors, or added as a component of an admixture of other receptors. Purified mGluR7 is also provided. Substantially pure mGluR7 of at least about 50% is preferred, at least about 70–80% more preferred, and 95–99% or more homogeneity most preferred, particularly for pharmaceutical uses. Once purified, partially or to homogeneity, as desired, the recombinant mGluR7 or native mGluR7 may then be used to generate antibodies, in assay procedures, etc.

In another aspect, the invention concerns polypeptides and fragments of mGluR7. Polypeptides and fragments of mGluR7 may be isolated from recombinant expression systems or may be synthesized by the solid phase method of Merrifield, *Fed. Proc.* 21:412 (1962), Merrifield, *J. Am. Chem. Soc.* 85:2149 (1963), or Barany and Merrifield, in *The Peptides*, vol. 2, pp. 1–284 (1979) Academic Press, NY, each of which are incorporated herein by reference, or by use of an automated peptide synthesizer. By "polypeptides" is meant a sequence of at least about 3 amino acids, typically 6 or more, up to 100–200 amino acids or more, including entire proteins. For example, the portion(s) of mGluR7 protein which binds ligand may be identified by a variety of methods, such as by treating purified receptor with a protease or a chemical agent to fragment it and determine which fragment is able to bind to labeled glutamate in a ligand blot. Alternatively, ligand-binding regions of mGluR7 proteins may be determined by sequence alignment of mGluR7 amino-terminal domains with those of bacterial leucine-, isoleucine-, and valine-binding proteins as described in O'Hara et al., *Neuron* 11:41–52 (1993), incorporated herein by reference. Polypeptides may then be synthesized and used as antigen, to inhibit ligand-mGluR7 interaction, etc. It should be understood that as used herein, reference to mGluR7 is meant to include the protein, polypeptides, and fragments thereof unless the context indicates otherwise.

In another aspect, the invention provides means for regulating the mGluR7-ligand interaction, and thus treating, therapeutically and/or prophylactically, a disorder which can be linked directly or indirectly to mGluR7 or to its ligands, such as glutamate and other endogenous excitatory amino acids. By mGluR7 ligand is meant a molecule capable of being bound by a ligand-binding domain of mGluR7, a mGluR7 analog, or chimeric mGluR7 which can be produced in accordance with procedures for producing chimeric receptors as generally described in U.S. Pat. No. 4,859,609, incorporated by reference herein. The ligand may be chemically synthesized or may occur in nature. Ligands may be grouped into agonists and antagonists. Agonists are those molecules whose binding to a receptor induces the response pathway within a cell. Antagonists are those molecules whose binding to a receptor blocks the response pathway within a cell. By virtue of having the receptor of the invention, agonists or antagonists may be identified which stimulate or inhibit the interaction of ligand with mGluR7. With either agonists or antagonists the metabolism and reactivity of cells which express the receptor are controlled, thereby providing a means to abate or in some instances prevent the disorder.

Thus, the invention provides screening procedures for identifying agonists or antagonists of events mediated by the ligand-mGluR7 interaction. Such screening assays may employ a wide variety of formats, depending to some extent on which aspect of the ligand/receptor/G protein interaction is targeted. For example, such assays may be designed to identify compounds which bind to the receptor and thereby block or inhibit interaction of the receptor with the ligand. Other assays can be designed to identify compounds which can substitute for ligand and therefore stimulate mGluR7-mediated intracellular pathways. Yet other assays can be used to identify compounds which inhibit or facilitate the association of mGluR7 to G protein and thereby mediate the cellular response to mGluR7 ligand.

In one functional screening assay, mammalian cell lines are used which express mGluR7 that is functionally coupled to a mammalian G protein. In this assay, compounds are screened for their relative affinity as receptor agonists or antagonists by comparing the relative receptor occupancy to the extent of ligand induced stimulation or inhibition of second messenger metabolism. Although stimulation of mGluR7 receptors (e.g., by L-AP4) inhibits cAMP production in transfected cells, the transduction mechanism is not well defined. Inhibition of cAMP could be the mechanism for L-AP4 mediated decreases in transmitter release, but it is also likely that alternative coupling mechanisms are involved. The decreases observed in cAMP in mGluR7-expressing BHK cells is consistent with the involvement of a Gi/Go protein. The possible mechanism of coupling is offered only by way of explanation, not limitation.

The screening procedure can be used to identify reagents such as antibodies which specifically bind to the receptor and not to other known members of the GluR family, i.e., mGluR1-mGluR6, and substantially affect its interaction with ligand, for example. The antibodies may be monoclonal or polyclonal, in the form of antiserum or monospecific antibodies, such as purified antiserum or monoclonal antibodies (e.g., murine, humanized, or completely human) or mixtures thereof. The antibodies which bind mGluR7 may be produced by a variety of well known methods.

In other embodiments, the invention provides screening assays conducted in vitro with cells which express the receptor. For example, the DNA which encodes the receptor or selected portions thereof may be transfected into an established cell line, e.g., a mammalian cell line such as BHK or CHO, using procedures known in the art (see, e.g., Sambrook et al., *Molecular Cloning, A Laboratory Manual*, 2d ed., Cold Spring Harbor Laboratory Press, Cold Spring Harbor, N.Y., 1989, which is incorporated herein by reference). The receptor is then expressed by the cultured cells, and selected agents are screened for the desired effect on the cell, separately or in conjunction with an appropriate ligand such as glutamate or L-AP4, for example. Means for amplifying nucleic acid sequences which may be employed to amplify the receptor or portions thereof are described in U.S. Pat. Nos. 4,683,195 and 4,683,202, incorporated herein by reference.

In yet another aspect, the screening assays provided by the invention relate to transgenic mammals whose germ cells and somatic cells contain a nucleotide sequence encoding mGluR7 protein or a selected portion of the receptor which, e.g., binds ligand, GTP binding protein, or the like. There are several means by which a sequence encoding, for example, the human mGluR7 may be introduced into a non-human mammalian embryo, some of which are described in, e.g., U.S. Pat. No. 4,736,866, Jaenisch, *Science* 240-1468–1474 (1988) and Westphal et al., *Annu. Rev. Cell Biol.* 5:181–196 (1989), which are incorporated herein by reference. The animal's cells then express the receptor and thus may be used as a convenient model for testing or screening selected agonists or antagonists.

In another aspect the invention concerns diagnostic methods and compositions. By having the mGluR7 molecule and antibodies thereto, a variety of diagnostic assays are provided. For example, antibodies (including monoclonal antibodies) to mGluR7 can be used to determine the presence and/or concentration of receptor in selected cells or tissues in an individual or culture of interest. These assays can be used in the diagnosis and/or treatment of diseases such as, for example, cerebral ischemia, Parkinsons, senile dementia and other cognitive disorders, Huntington's chorea, amyotrophic lateral sclerosis, migraine, and others.

Numerous types of immunoassays and histological techniques are available and can be used to identify mGluR7 on the surface of cells. See generally, Harlow and Lane, *Antibodies, A Laboratory Manual*, Cold Spring Harbor Publications, N.Y. (1988), and Cuello, *Immunohistochemistry*, John Wiley & Sons, N.Y. (1984), each incorporated by reference herein. In one assay format mGluR7 is identified and/or quantified by using labeled antibodies, preferably monoclonal antibodies which are reacted with olfactory bulb or brain tissues, e.g., cortex, striatum, hippocampus, cerebellum, and determining the specific binding thereto, the assay typically being performed under conditions conducive to immune complex formation. Unlabeled primary antibody can be used in combination with labels that are reactive with primary antibody to detect the receptor. For example, the primary antibody may be detected indirectly by a labeled secondary antibody made to specifically detect the primary antibody. Alternatively, the anti-mGluR7 antibody can be directly labeled. A wide variety of labels may be employed, such as radionuclides, particles (e.g., gold, ferritin, magnetic particles, red blood cells), fluorophores, chemiluminescers, enzymes, enzyme substrates, enzyme cofactors, enzyme inhibitors, ligands (particularly haptens), etc.

The mGluR7 DNA may be directly detected in cells with a labeled mGluR7 DNA or synthetic oligonucleotide probe in a hybridization procedure similar to the Southern or dot blot. Also, the polymerase chain reaction (Saiki et al., *Science* 239:487 (1988), and U.S. Pat. No. 4,683,195) may be used to amplify DNA sequences, which are subsequently detected by their characteristic size on agarose gels, Southern blot of these gels using mGluR7 DNA or a oligonucleotide probe, or a dot blot using similar probes. The probes may comprise from about 14 nucleotides to about 25 or more nucleotides, preferably, 40 to 60 nucleotides, and in some instances a substantial portion or even the entire cDNA of mGluR7 may be used. The probes are labeled to provide a detectable signal, such as with an enzyme, biotin, a radionuclide, fluorophore, chemiluminescer, paramagnetic particle, etc.

Kits can also be supplied for use with the receptor of the subject invention in the detection of the presence of the receptor or antibodies thereto, as might be desired in the case of autoimmune disease. Thus, antibodies to mGluR7, preferably monospecific antibodies such as monoclonal antibodies, or compositions of the receptor may be provided, usually in lyophilized form in a container, either segregated or in conjunction with additional reagents, such as antiantibodies, labels, gene probes, polymerase chain reaction primers and polymerase, and the like.

The following examples are offered by way of illustration of the invention and not by limitation.

Example I cDNA Cloning and Sequencing of mGluR7

This Example describes screening a rat olfactory bulb cDNA library and identification of a metabotropic receptor designated "mGluR7".

Degenerate oligonucleotide primers were used to amplify a region of first strand olfactory bulb cDNA between transmembrane region II and intracellular loop III of mGluR cDNAs. The sequence of the 5' primer was GC(TCAG)GG (TCAG)AT(ACT)TT(CT)(CT)T(TCAG)(GT)G(TCAG) (SEQ ID NO:4) and the 3' primer was AT(TCAG)(GT)(AG) (CT)TT(TCAG)GC(CT)TC(AG)TT(AG)AA (SEQ ID NO:5). The 5' ends of both primers also contained sequences for an EcoRI restriction site. The PCR samples were analyzed by agarose gel and amplified fragments of approximately 350 basepairs were digested with EcoRI and cloned into pBluescript II KS (+) Stratagene Cloning Systems, La Jolla, Calif. Of sixty-five clones initially identified, three PCR products (Olf 1, 2 and 8) were identified as unique receptors, shown by DNA sequence analysis (Sanger et al., *Proc. Natl. Acad. Sci. USA* 74: 5436–5367 [1977]) to be distinct from previously isolated mGluR cDNAs.

The Olf 1, 2 and 8 clones were used as template to generate $^{32}$P-labeled in vitro RNA transcripts. These were equally mixed and used to probe an adult rat olfactory bulb cDNA library (Stratagene, La Jolla, Calif.). Twenty-four duplicate positive clones were rescued by coinfection with helper bacteriophage into pBluescript SK (–) Stratagene Cloning Systems, La Jolla, Calif.; fourteen had cDNA inserts as shown by restriction analysis. Southern blot analysis (Southern, *J. Mol. Biol.* 98: 503–517 [1975]) with Olf 1, 2 or 8 identified three distinct groups of clones: Olf 1 labeled 10 clones identified as mGluR5 (Abe et al., *J. Biol. Chem.* 267: 13361–13368 [1992]). Olf 8 identified 3 clones that also showed unique DNA sequence related to the mGluR family. Olf 2 labeled a single clone that appeared to be a new member of the mGluR family. The full-length clone isolated with Olf 2 was designated "mGluR7."

The nucleotide sequence and predicted amino acid sequence for mGluR7 is shown in FIG. 1 SEQ ID NO:1. The cDNA sequence contained an open reading frame of 2745 bp and an initiation codon consensus sequence surrounding the presumed initiator methionine (Kozak, *Nucl. Acids Res.* 15:

8125–8148 [1987]). The deduced amino acid sequence of mGluR7 is 915 amino acids with an estimated molecular weight of 125,126 kD. Hydrophobicity analysis (Kyte and Doolittle, *J. Mol. Biol.* 157: 105–132 [1982]) indicates a seven transmembrane-domain receptor with the characteristic features of the metabotropic receptors, including a large amino-terminus domain of 590 amino acids and a large second cytoplasmic loop that appears to be involved in coupling of mGluRs to G proteins (Pin, *Func. Neurol.* supp. 8: 42 [1993]). There are four putative N-glycosylation sites in the amino terminus and one putative calcium/calmodulin-dependent protein kinase II phosphorylation site in the second intracellular domain.

Amino acid sequence comparison of mGluR7 and other members of the mGluR family showed a high degree of conservation with mGluR4 (69%) and mGluR6 (67%), with a lower degree of conservation with mGluR1 (42%), mGluR2 (45%), mGluR3 (45%) or mGluR5 (45%). These overall homologies place mGluR7 into a subset of mGluRs that includes mGluR4 and mGluR6.

Example II

Expression of mGluR7

BHK cells were transfected with mGluR7 subcloned into pZEM229R. Plasmid pZEM229R is a pUC18-based expression vector containing an EcoRI cloning site between a mouse metallothionein-I promoter and an SV40 transcription terminator. The vector also contains an expression unit of the SV40 early promoter, mouse dihydrofolate reductase gene, and SV40 terminator. The two expression units are in opposite orientations with their respective promoters adjacent to each other. *E. coli* HB101 transformed with pZEM229R was deposited with American Type Culture Collection, 12301 Parklawn Drive, Rockville, MD on Sep. 28, 1993.

The cells were grown in 10% fetal calf serum and Dulbecco's minimal essential media (DMEM), and transfected clones were selected by methotrexate resistance. Resistant clones were assayed for the presence of mGluR7 RNA and protein. Confluent cells were assayed for cAMP production (Amersham) in the presence of IBMX (1 mM) isobutylmethylxanthine; cAMP levels were measured after 10 minute treatment with forskolin (10 $\mu$M) in the presence or absence of mGluR agonists or antagonists. Assays were performed in triplicate three times and the average value from these experiments expressed as the mean cAMP levels plus and minus the standard deviation. The basal cAMP production was subtracted from the stimulated levels and the inhibition was plotted as a percent of the forskolin-stimulated control.

For oocyte expression studies, xenopus laevis (Xenopus I, Ann Arbor) were anesthetized with tricaine and oocytes harvested using sterile technique. RNA transcripts from mGluR1 and mGluR7 were injected into Stage V–VI oocytes (1–100 ng RNA/oocyte) and the oocytes were assayed for production of a calcium-activated chloride current using a two-electrode voltage clamp. Harvesting of oocytes, solutions and recording methods were as described by Lester and colleagues (Dascal et al., *Brain Res.* 387: 201–209 [1986], which is incorporated herein by reference).

In several experiments, oocytes injected with mGluR7 mRNA evoked no glutamate responses, despite large calcium-activated chloride currents in sister oocytes injected with mGluR1 mRNA. These data suggested that mGluR7, unlike mGluR1 and mGluR5 (Masu et al., *Nature* 349: 760–765 [1991]; Houamed et al., *Science* 252: 1318–1321 [1991]; and Abe et al., *supra*), does not activate phospholipase C.

Other metabotropic receptors (mGluR2-4 and mGluR6) have been shown to inhibit cAMP production in Chinese hamster ovary (CHO) cells (Tanabe et al., *Neuron* 8: 169–179 [1992]; Tanabe et al., *J. Neurosci.* 13: 1372–1378 [1993]; and Nakajima et al., *J. Biol. Chem.* 268: 11868–11873 [1993]), or BHK cells (Thomsen et al., *Eur. J. Pharmacol.* 227: 361–362 [1992]). As shown in FIG. 2, L-AP4 (1 mM) or glutamate (1 mM) inhibited forskolin-stimulated cAMP production in BHK cells stably expressing mGluR7 cDNA, confirming that mGluR7 is a member of the metabotropic receptor family. The presence of mGluR7 in the transfected BHK cells was confirmed by RNA blot, and by immunoblot analysis using a polyclonal antisera prepared against an mGluR7 peptide representing amino acids 896–909 of mGluR7 (Val-Asp-Pro-Asn-Ser-Pro-Ala-Ala-Lys-Lys-Lys-Tyr-Val-Ser-SEQ ID NO:3).

L-AP4 had no significant effect on basal cAMP levels or on forskolin-stimulated cAMP levels in wild-type BHK cells. Lower concentrations of L-AP4 (100 $\mu$M) or glutamate (100 $\mu$M) produced small decreases in cAMP which were not statistically significant. ACPD (1 mM) or quisqualate (0.5 mM) were much less effective at concentrations far in excess of those that result in maximal stimulation of mGluR1. Likewise, 2-amino-3-phosphonopropionic acid (L-AP3; 3 mM) or RS-$\alpha$-methyl-4-carboxyphenylglycine (MCPG; 1 mM) that antagonize mGluR1 in some preparations did not antagonize mGluR7-mediated cAMP inhibition. L-AP4 (1 mM) stimulation of a BHK clone expressing mGluR4 produced 45% inhibition, confirming the sensitivity of the assay. Although the submaximal inhibition of CAMP by mGluR7 obtained prevented full concentration-response analysis, L-AP4 and glutamate were much less potent agonists of mGluR7 in these experiments than has previously been observed for mGluR4 or mGluR6. The modest inhibition at lower levels of agonist observed in these experiments may be due either to lower levels of receptor expression or to less efficient coupling to adenylate cyclase for mGluR7. cAMP inhibition may not be the principal transduction mechanism for mGluR7 in neurons, as mGluR6 inhibits cAMP in CHO cells, but its primary action in neurons is likely to be stimulation of a phosphodiesterase (Nawy and Jahr, *Nature* 346: 269–271 [1990]).

Example III

Distribution of mGluR7 RNA

A mGluR7 cDNA probe was hybridized to poly (A)+RNA isolated from several regions of adult rat brain to determine distribution of mGluR7 RNA. Total RNA was isolated from freshly dissected rat brain regions representing cerebellum, hippocampus, hypothalamus, olfactory bulb, brainstem, midbrain, thalamus, and cortex as described (Chomczynski and Sacchi, *Anal. Biochem.* 162: 156–159 [1987]). Poly (A)+RNA was isolated using a magnesphere RNA isolation kit (Promega). Two micrograms of poly(A)+RNA sample were fractionated by denaturing agarose gel electrophoresis and capillary transferred to nitrocellulose, followed by hybridization with a random-primed $^{32}$P-labeled 719 bp XhoI fragment containing nucleotides 1–197 of the mGluR7 cDNA and a 1234 bp XhoI/PstI fragment of mGluR4 containing nucleotides 791–2025.

Hybridization of a mGluR7 cDNA probe to poly (A)+ RNA isolated from several regions of adult rat brain revealed a single class of messenger RNA of approximately 4.4 Kb. The previously identified L-AP4-sensitive receptors mGluR4 and mGluR6 show quite constricted patterns of RNA expression. However, mGluR7 was widely expressed in the CNS. Highest expression was seen in the thalamus, neocortex and hypothalamus, with significant levels of expression in the hippocampus, olfactory bulb, brainstem and midbrain.

For in situ hybridization, adult Sprague-Dawley rats (200–250 g) were anesthetized with pentobarbital and perfused transcardially with ice-cold saline, followed by ice-cold fixative (4% paraformaldehyde/0.1 M sodium borate, pH 9.5). The brains were post-fixed overnight in fixative containing 10% sucrose. Sections (25 µm) were mounted on gelatin- and poly-L-lysine-coated glass, fixed for 15 minutes in 4% paraformaldehyde/0.1 M phosphate buffered saline (PBS), washed twice in 0.1 M PBS, and treated for 30 min at 37° C. in proteinase K (0.001% in 0.1 M Tris/0.05 M EDTA, pH 8) followed by 0.0025% acetic anhydride in 0.1 M triethanolamine at room temperature followed by dehydration. A 719 bp XhoI fragment containing nucleotides 1–197 of mGluR7 and a 1234 bp XhoI/PstI fragment of mGluR4 containing nucleotides 791–2025 were subcloned into pBluescript KS(+). $^{35}$S-labeled antisense RNA was transcribed from each template and used for hybridization at $10^7$ cpm/ml for 20 hours at 58° C. in hybridization buffer (Mountjoy et al., Science 257: 1248–1251 [1992]). Slides were processed as described (Simerly and Young, Mol. Endocrinol. 5: 424–432 [1991]) then dipped in NTB-2 liquid photographic emulsion (Kodak), exposed for 13 days, developed with D-19 developer and counterstained with thionin.

In situ hybridization with a mGluR7 probe was consistent with the RNA blot analysis showing a broad distribution of hybridization in cortex, olfactory bulb, hippocampus, thalamus and caudate putamen, but with relatively low signal in the cerebellum. The distribution of mGluR7 was more widespread than mGluR4.

Comparison of mGluR7 with mGluR4 revealed complementary patterns of hybridization in the hippocampus and olfactory bulb, although both were highly expressed in the entorhinal cortex, subiculum and presubiculum. There was strong hybridization of mGluR7 in the dentate gyrus and hippocampus (CA1–CA4) and in the mitral/tufted cells of the olfactory bulb. By contrast, mGluR4 was present in the glomerular and granular cell layers of the olfactory bulb. In the cerebellum, mGluR4 mRNA was present in the granular layers while mGluR7 was restricted to the Purkinje cells.

The existence of multiple metabotropic receptors with distinct, but overlapping patterns of distribution suggested that single cells may contain more than one mGluR subtype. This was tested in the olfactory bulb by a double labeling method using probes for mGluR7 and mGluR1. For double labeling, mGluR1probes were labeled with digoxigenin-UTP as above whereas mGluR7 probes were labeled with $^{35}$S-UTP. Digoxigenin-labeled in vitro RNA transcripts for mGluR1 were generated from a 1363 bp EcoRI/SacI cDNA fragment containing nucleotides 361–1724 of mGluR1 (Masu et al., Nature 349: 760–765 (1991)). Sections were incubated with both probes, reacted for digoxigenin and processed as above. After incubation overnight in 2X SSC/0.05% Triton X-100/2% normal goat serum, sections were incubated with anti-digoxigenin alkaline phosphatase conjugate diluted 1:1000 in 0.1 M Tris-HCl pH 7.5/0.15 M NaCl/0.3% Triton X-100/1% normal goat serum for 5 hrs, followed by incubation overnight in the dark in 0.1 M Tris-HCl pH 9.5/0.1 M NaCl/0.05 M MgCl$_2$ containing 337.5 mg/ml 4-nitro blue tetrazolium chloride/175 mg/ml 5-bromo-4-chloro-3-indolyl-phosphate/300 mg/ml levamisole. The reaction was stopped with 0.01 M Tris-HCl pH 8.1/1 mM EDTA, followed by rapid dehydration in increasing concentrations of ethanol containing 0.1X SSC/1mM dithiothreitol. After vacuum drying, slides were dipped in Ilford K.5 photographic emulsion and exposed for 13 days, followed by development with D-19. Slides were not counter-stained.

Most mitral/tufted cells were labeled with mGluR7 as represented by the silver grains. Likewise all the mGluR7 labeled cells were also labeled with mGluR1using digoxigenin as the chromogen. The sections were not counter-stained and thus the diffuse staining of the soma represents the digoxigenin reaction product. The mGluR1 has been localized to both postsynaptic and presynaptic locations (Martin et al., Neuron 9: 259–270 (1992) and unpublished data) whereas the effects of L-AP4 on mitral/tufted cells is presynaptic (Trombley and Westbrook, J. Neurosci. 12: 2-43-2050 (1992)). This may suggest a compartmentalization of different mGluR subtypes within the same neuron. Thus, the L-AP4-sensitivity and expression pattern of mGluR7 suggest that it is a presynaptic autoreceptor in selected CNS pathways.

All publications and patents mentioned in this specification are herein incorporated by reference into the specification to the same extent as if each individual publication or patent was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. Isolated and purified metabotropic glutamate receptor protein which has the amino acid sequence shown in SEQ ID NO:2 or a polypeptide comprising at least 100 contiguous amino acids thereof.

2. An isolated polynucleotide molecule which codes for a metabotropic glutamate receptor protein which has the amino acid sequence shown in SEQ ID NO:2 or a polypeptide comprising at least 100 contiguous amino acids of said protein.

3. The polynucleotide molecule of claim 2, which encodes a polypeptide displaying mammalian G protein-coupled glutamate receptor activity.

4. The polynucleotide molecule of claim 2, wherein the polynucleotide has the sequence as shown in FIG. 1 (SEQ ID NO: 1), from nucleotide 94 to nucleotide 2745.

5. A DNA construct comprising the following operably linked elements:

a transcriptional promoter;

an isolated DNA molecule encoding a metabotropic glutamate receptor protein which has the amino acid sequence shown in SEQ ID NO:2 or a polypeptide comprising at least 100 contiguous amino acids of said protein; and a transcriptional terminator.

6. The DNA construct of claim 5, wherein the DNA molecule encodes the mGluR7 amino acid sequence of FIG. 1 (SEQ ID NO:2).

7. A cultured eukaryotic cell transformed or transfected with a DNA construct which comprises the following operably linked elements:

a transcriptional promoter;

an isolated DNA molecule encoding a metabotropic glutamate receptor protein which has the amino acid sequence shown in SEQ ID NO:2 or a polypeptide comprising at least 100 contiguous amino acids of said protein; and a transcriptional terminator.

8. The eukaryotic cell of claim 7, which is a mammalian cell.

9. The eukaryotic cell of claim 8, which does not express endogenous G protein coupled glutamate receptors.

10. The eukaryotic cell line of claim 9, wherein the mGluR7 polypeptide encoded by the DNA molecule is coupled to G protein in the mammalian cell.

11. A method for identifying a compound which alters metabotropic glutamate receptor mediated-metabolism, which comprises incubating the compound with eukaryotic cells which express recombinant metabotropic glutamate receptor protein which has the amino acid sequence shown in SEQ ID NO:2, wherein said metabotropic glutamate receptor protein is activated by L-2-amino-4-phosphonobutryic acid (L-AP4) to inhibit stimulation of intracellular cAMP production, and determining therefrom the effect of said compound on metabotropic glutamate receptor-mediated metabolism in the cells.

12. The method of claim 11, wherein the compound is incubated with the receptor and ligand.

13. The method of claim 12, wherein the ligand is glutamate or L-AP4.

14. The method of claim 11, wherein cyclic AMP production in the eukaryotic cell is monitored for alteration by the compound.

* * * * *